United States Patent [19]

Kuenecke et al.

[11] Patent Number: 5,196,008

[45] Date of Patent: Mar. 23, 1993

[54] METHOD AND CIRCUIT FOR MONITORING ELECTRODE SURFACES AT THE BODY TISSUE OF A PATIENT IN AN HF SURGERY DEVICE

[75] Inventors: Peter Kuenecke, Buckenhof; Uwe Hagen, Forchheim, both of Fed. Rep. of Germany

[73] Assignee: Siemens Aktiengesellschaft, Munich, Fed. Rep. of Germany

[21] Appl. No.: 571,124

[22] Filed: Aug. 23, 1990

[30] Foreign Application Priority Data

Sep. 7, 1989 [EP] European Pat. Off. ........ 89116573.0

[51] Int. Cl.$^5$ .............................................. A61B 17/39
[52] U.S. Cl. .......................................... 606/35; 606/32
[58] Field of Search ...................................... 606/35, 32

[56] References Cited

U.S. PATENT DOCUMENTS 4,416,276  11/1983  Newton et al. .
4,416,277  11/1983  Newton et al. .
4,754,757  7/1988   Feucht .
4,770,173  9/1988   Feucht et al. ........................ 606/32

FOREIGN PATENT DOCUMENTS 3206947  9/1983  Fed. Rep. of Germany ........ 606/32

Primary Examiner—Lee S. Cohen
Attorney, Agent, or Firm—Hill, Van Santen, Steadman & Simpson

[57] ABSTRACT

A method for monitoring a number of electrode surfaces of an electrode of the type used in an HF surgery device includes the steps, in a first stage of the method, of connecting one of the electrode surfaces to a current source and connecting a measuring unit via a first switch to at least two of the remaining electrode surfaces to be monitored and thereby forming measured values which are to be compared to each other for equality. In a second stage of the method, a different electrode surface is connected to the current source and the measuring unit is connected to different ones of the remaining electrode surfaces, and measured values are again obtained and compared for quality. The electrode surface which served as the auxiliary (i.e., current supplied) electrode in the first stage of the method may serve as one of the monitored electrode surfaces in the second stage. A circuit for practicing the method is also disclosed.

11 Claims, 1 Drawing Sheet

METHOD AND CIRCUIT FOR MONITORING ELECTRODE SURFACES AT THE BODY TISSUE OF A PATIENT IN AN HF SURGERY DEVICE

BACKGROUND OF THE INVENTION

1. Field of the Invention

The present invention is directed to a method and circuit for monitoring a number of electrode surfaces of the neutral electrode of an HF surgery device to determine whether the surfaces are in planar adjacency against the body tissue.

2. Description of the Prior Art

In HF surgery devices, partial detachment of the neutral electrode can result in burning of the patient, and therefore methods and circuits are known to monitor the plurality of electrode surfaces (sub-electrodes) which are present as part of the neutral electrode to determine if those surfaces are in planar adjacency against the body tissue of the patient. In such known methods and circuits, a source current (auxiliary current) is applied to one of the electrode surfaces (auxiliary electrode) which is in contact with the body tissue of the patient in an electrically conductive fashion. The resulting current is measured at two other electrode surfaces, which are also in contact with the body tissue of the patient in an electrically conductive fashion. If one of the measured currents exceeds a permissible deviation toward a higher or lower current in comparison to the other electrode, an alarm signal is generated, which may automatically disconnect the surgery device. The permissible deviation may be exceeded, for example, due to partial detachment of an electrode surface from the patient. If, however, two electrode surfaces detach simultaneously so that the remaining surfaces of the respective electrodes in contact with the patient have approximately the same area, the resulting currents which are measured will still be approximately the same, and thus the monitoring circuit will not be able to determine that such partial detachment has occurred.

Solutions to this problem are known which attempt to minimize the risk of the formation of residual electrode surfaces of identical size occurring upon partial detachment of the neutral electrode. For example, the number of electrode surfaces may be increased and/or the electrode surfaces may be provided with a special shape. A disadvantage of all known methods and circuit arrangements, however, is that the auxiliary electrode itself cannot be used as an electrode which is monitored to determine the existence of detachment.

SUMMARY OF THE INVENTION

It is an object of the present invention to provide a method and circuit for monitoring electrode surfaces at the body tissue of a patient in an HF surgery device which permit the auxiliary electrode to be used as one of the electrodes which is monitored to determine the existence of partial detachment of the neutral electrode from the body tissue of the patient.

The above object is achieved in accordance with the principles of the present invention in a method for monitoring a plurality of electrode surfaces of a neutral electrode of an HF surgery device for planar adjaceny against the body tissue of a patient wherein current from a current source is supplied to a first electrode surface, the resulting current values are measured at all, or at least at some, of the remaining electrode surfaces, at least two of the measured values are checked for equality, and upon the occurrence of a permissible deviation of the measured values being exceeded, an alarm signal is generated. The foregoing takes place in a first stage of the method. In a second stage of the method, the current from the current source is supplied to another electrode surface, other than the first electrode surface, and the resulting current values are again measured at all, or at least at some, of the remaining electrode surfaces, these remaining electrode surfaces now including the first electrode surface. At least two of the measured values are again checked for equality, and an alarm signal is generated if the permissible deviation is exceeded.

In an apparatus constructed in accordance with the principles of the present invention, for practicing the above method, at least measuring unit is provided which is connectable, via a first switching stage, to each of the plurality of electrode surfaces on the neutral electrode. A current source, which supplies a measurement current, is connectable to each of the electrode surfaces, one at a time, via a second switching stage. The first and second switching stages are designed so that an electrode surface which is connected to the current source via the second switching stage will not simultaneously be connected to the measuring unit via the first switching stage. An electronic control circuit operates the first and second switching stages to cycle through, in chronological succession, the plurality of connections to each of the electrode surfaces.

In a first embodiment of the circuit, the second switching stage connects the electrode surfaces one at a time to the measuring unit. When current is supplied to one electrode surface from the current source via the second switching stage, the first switching stage will conduct the resulting current from another of the electrode surfaces to a measuring unit wherein its value is measured. This value is then stored in an evaluation unit. An electronic control unit then switches the state of the second switching stage so that a different electrode surface is connected to the measuring unit, and the resulting current is again measured and supplied to the evaluation unit. A comparison is undertaken in the evaluation unit and if a permissible deviation between the stored current value and the latest current value is exceeded, an alarm signal is generated. The electronic control unit then switches the second switching stage so that the measurement current is supplied to a different electrode surface, and the cycle is repeated.

In a second embodiment of the circuit, the first switching stage is provided with two banks of switches, respectively connected to two measuring units. The switches in each bank are connected to the electrode surfaces. During a measurement, current is supplied from the current source to one of the electrode surfaces, and the resulting currents from two of the other electrode surfaces are respectively supplied to the measuring units via the respective banks of the first switching stage. A comparison of these simultaneously acquired currents is then undertaken in the evaluation unit, and again if a permissible deviation is exceeded, an alarm signal is generated.

In the method and circuit in accordance with the principles of the present invention, each electrode surface briefly serves as the auxiliary electrode, but that electrode surface is not prevented from subsequently serving as one of the electrode surfaces which is monitored to determine the existence of a partial detachment of the neutral electrode. The method and circuit disclosed herein therefore considerably increase the reliability against accidental detachment of the electrode surface being undetected, and therefore minimize the undesired side effects of such an undetected detachment, such as burning the patient, particularly during an HF surgical operation.

DESCRIPTION OF THE PREFERRED EMBODIMENTS

Figure 1:
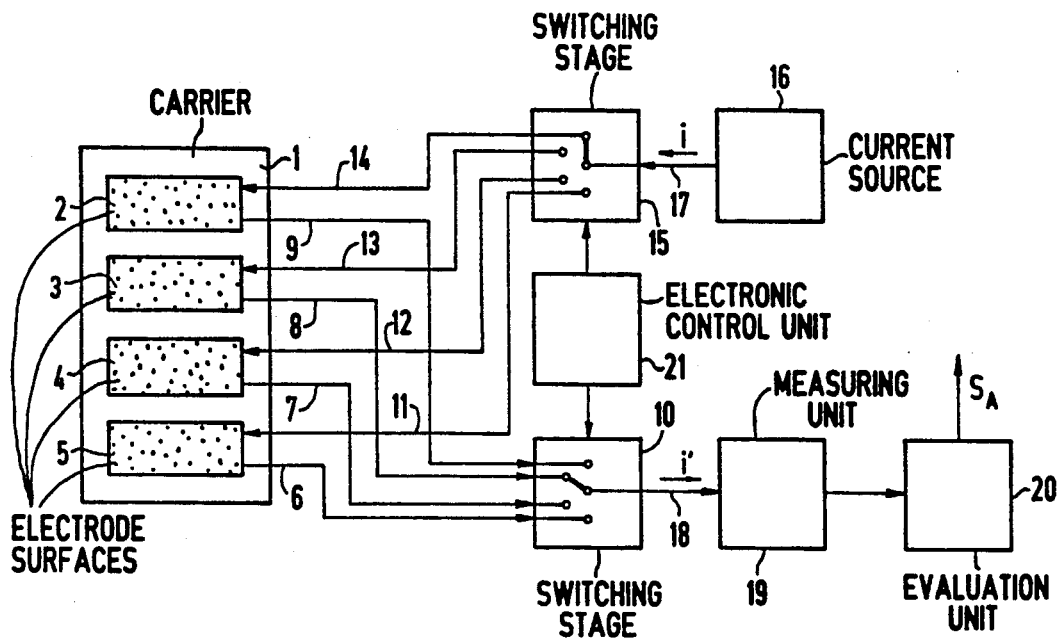
FIG. 1 is a schematic block diagram of a first embodiment of a circuit constructed in accordance with the principles of the present invention for practicing the method disclosed herein.

As shown in FIG. 1, a neutral electrode, of the type suitable for use in an HF surgery device, has four electrode surfaces 2, 3, 4 and 5, arranged on a common, flexible carrier 1. The electrode surfaces 2 through 5 are respectively connected via lines 6, 7, 8 and 9 to a first switching stage 10, and are respectively connected via lines 11, 12, 13 and 14 to a second switching stage 15. A current source 16 is provided which supplies a high-frequency alternating current i to the input terminal of the second switching stage 15 via a line 17. For simplicity, the arrow indicating the direction of flow for the current i is shown as if the current were direct current, however, it will be understood that since the current i is a high-frequency alternating current, its direction of current flow will be constantly changing. With the second switching stage 15 in the state shown in the exemplary embodiment of FIG. 1, the current i is supplied to the electrode surface 2.

When the electrode surfaces 2 through 5 are disposed against the body tissue of a patient, in electrical contact with the body tissue, current will flow from the electrode surface connected to the current source, such as the electrode surface 2, to each of the other electrode surfaces. One of the other electrode surfaces, such as the electrode surface 3 in the embodiment of FIG. 1, is connected via the first switching stage 10 to a measuring unit 19 so that the resulting measured current i' (again indicated for simplicity, with a unit directional arrow) is supplied to the measuring unit 19. The current source 16 and the measuring unit 19 are electrically connected together, in a manner not shown in FIG. 1, to form a closed circuit.

The first and second switching stages are designed so that an electrode surface which is connected to the current source 16 will not simultaneously be connected to the measuring unit 19.

The value of the resulting current i', measured in the measuring unit 19, is supplied to an evaluation unit 20, and is stored therein a memory (not separately shown). An electronic control unit 21 subsequently switches the first switching stage 10 so that another of the electrode surfaces, other than the electrode surface being supplied with current from the current source 16, is connected to the measuring unit 19. The state of the second switching stage remains unchanged at this time. A further resulting current i' is the obtained and is measured in the measuring unit 19, and is supplied to the evaluation unit 20, wherein the latest resulting current is compared for equality with the previously stored value. If a permissible deviation of the two measured values is exceeded, an alarm signal $S_A$ is generated which may activate an audio or visual alarm and may simultaneously automatically interrupt the surgical procedure.

The measured value from the electrode surface 3, which was previously stored, is then erased in the evaluation unit 20, and the latest measured value is stored in its place. The electronic control unit 21 then switches the first switching stage 10 so that another electrode surface, from a measurement has not yet been obtained, is connected to the measuring unit 19. The same sequence of measuring, comparing, erasing and storing is then repeated. In the embodiment of FIG. 1 having four electrode surfaces, with one of the electrode surfaces (electrode surface 2) temporarily serving as the auxiliary electrode, permits inequalities in the contacting are between electrodes 3 and 4 to be measured, as well as inequalities in area between the electrode surfaces 4 and 5. The sequence of step to this point constitutes a first stage of the method.

In a second stage of the method, the electronic control unit 21 operates to switch the state of second switching stage 15 so that a different electrode surface is supplied with the source current i from the current source 16 so that a different electrode surface, such as the electrode surface 3, serves as the auxiliary electrode. The electrode surface 2 is then free to serve as one of the electrode surfaces which is monitored, using the sequence described above, for surface area equality with the other electrode surfaces.

In the exemplary embodiment of FIG. 1, all electrodes 2 through 5 can be successively used as the auxiliary electrode in a measuring cycle by operation of the second switching stage 15. It is also possible, however, to operate the second switching stage 15 so that only two of the electrode surfaces 2 through 5 are alternatingly used as the auxiliary electrode.

Although the switching stages 10 and 15 are schematically shown with a wiper movable among a number of contacts, it will be understood that the switching stages are actually electronic switching stages, and the switches can be operated in any desired sequence by the electronic control unit 21.

The measuring unit 19 is preferably an impedance measuring unit with which measurement of the magnitude and phase angle of the resulting currents i' can be undertaken so that the impedance of the body tissue of the patient between two of the electrode surfaces which are respectively connected to the current source 16 and the measuring unit 19 can be measured.

Figure 2:
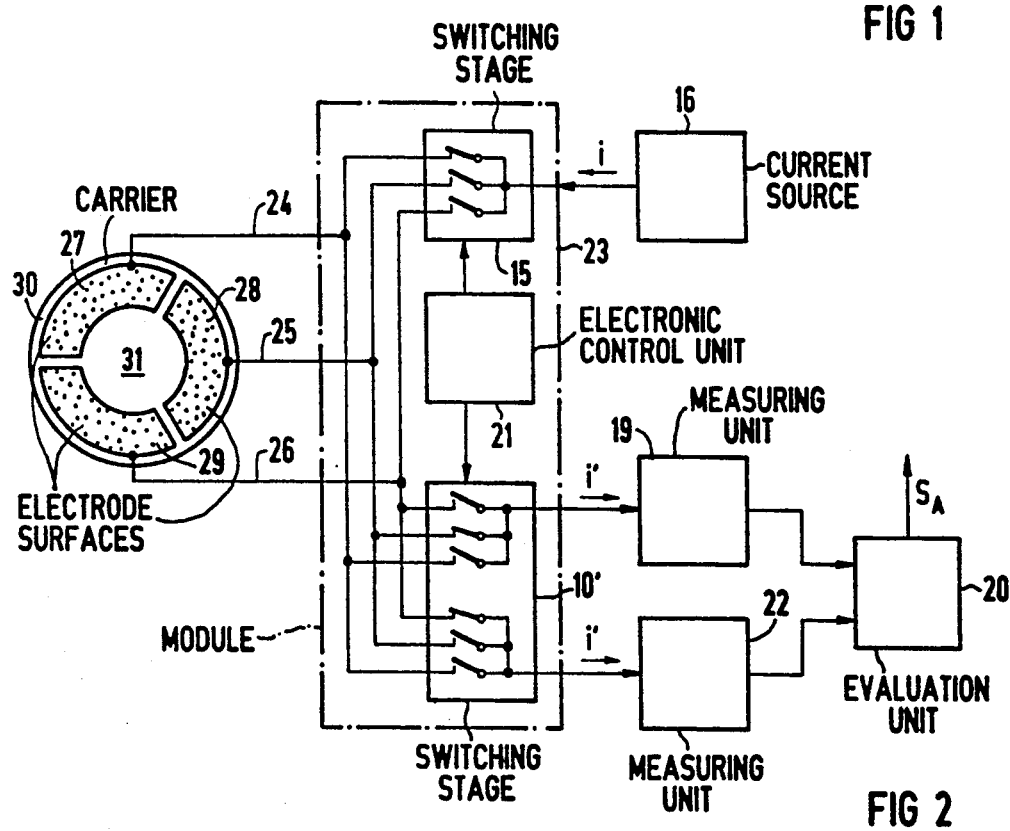
FIG. 2 is a schematic block diagram of a second embodiment of a circuit constructed in accordance with the principles of the present invention for practicing the method disclosed herein.

The embodiment of FIG. 2 differs from the embodiment of FIG. 1 in that two measuring units 19 and 22 are connected to the evaluation unit 20. In this embodiment, the evaluation unit 20 does not contain a memory for a preceding measured result, because the two measuring units 19 and 20 respectively simultaneously supply a measured result to the evaluation unit 20. For this purpose, the first switching stage 10' has two switching banks respectively connected to the measuring units 19 and 22.

The first switching stage 10', the second switching stage 15 and the electronic control unit 21 in the embodiment of FIG. 2 are combined in a single structural unit or module 23. The neutral electrode in this embodiment is formed by three annular electrode surfaces 27, 28 and 29 disposed on a flexible carrier 30. The carrier 30 has a central circular area 31 which is free of electrode surfaces. Only one electrical line leads from the module 23 to each of the electrode surfaces, these lines being 24, 25 and 26. As a result of the symmetrical arrangement of the electrode surfaces 27, 28 and 29, the permissible deviation of the measured values can be maintained very small, and thus patient safety can be further increased.

In the embodiment of FIG. 2, the current source 16 is connected via the second switching stage 15 and line 24 to the electrode surface 27, which forms the auxiliary electrode in the first stage of the method. The other two electrode surfaces 28 and 29 are each connected via the switching banks of the first switching stage 10' to respective measuring units 19 and 22.

After a comparison of the simultaneously supplied measured results in the evaluation unit 20, the electronic control unit 21 switches the current source 16 to connect a different electrode surface, such as electrode surface 28 to the current source 16 via the line 25. At the same time, the electronic control unit 21 changes the state of the first switching stage 10' so that the electrode surfaces 27 and 29 are respectively connected to the measuring units 19 and 22 via respective lines 24 and 26. In contrast to the first stage of the method described above. The electrode surface 28 is now connected as the auxiliary electrode in this second stage of the method. In the second stage of the method, the electrode surface 27, which was previously connected as the auxiliary electrode in the first stage of the method, now serves as one of the monitoring electrode surfaces together with the electrode surface 29. The first and second stages of the method form a measuring cycle which can be repeated as soon as the measured results from the two measuring units 19 and 22 have been evaluated in the evaluation unit 20. The electronic control unit 21 can then change the state of the first switching stage 10' and the second switching stage 15 back to the illustrated switch position.

The monitoring possibilities, and thus patient safety, can be further enhanced by adding a third stage to the method, wherein the electrode surface 29 is connected to the current source 16 via the second switching stage 15 and the line 26, so as to serve as the auxiliary electrode. In this third stage of the method, the electrode surfaces 27 and 28 are connected to the respective measuring units 19 and 22 via the first switching stage 10' and respective lines 24 and 25. The third stage of the method, which forms a measuring cycle in combination with the two preceding stages of the method, ends after two simultaneously acquired measured results from the measuring units 19 and 22 are compared in the evaluation unit 20. At the end of this third stage of the method, the electronic control unit 21 changes the state of the first switching stage 10' and the second switching stage 15 back to the illustrated switch position, thereby initiating a second measuring cycle having a sequence of stages corresponding to that of the first measuring cycle.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for monitoring a neutral electrode in an HF surgery device, said neutral electrode having a plurality of electrode surfaces, for planar adjacency against body tissue of a patient, said method comprising the steps of:
   (a) connecting a first of said electrode surfaces to a current source thereby causing a voltage to arise of each of the remaining electrode surfaces;
   (b) measuring the resulting current caused by said voltage at at least two of said remaining electrode surfaces;
   (c) comparing the resulting currents at said at least two remaining electrode surfaces for equality;
   (d) generating an alarm signal if said resulting currents at said at least two remaining electrode surfaces differ by more than a predetermined deviation;
   (e) connecting a second of said electrode surfaces to said current source thereby causing further resulting currents to arise at each of the further remaining electrode surfaces, said further remaining electrode surfaces including said first electrode surface;
   (f) measuring the further resulting current at at least two of said further remaining electrode surfaces;
   (g) comparing the further resulting currents at said at least two further remaining electrode surfaces for equality; and
   (h) generating an alarm signal if said further resulting currents at said at least two further remaining electrode surfaces differ by more than said predetermined deviation.

2. A method as claimed in claim 1 comprising the additional steps of:
   defining a measuring cycle as the successive connection of at least two of said electrode surfaces to said current source; and
   successively repeating said measuring cycle.

3. A method as claimed in claim 1 comprising the additional steps of:
   defining a measuring cycle as the successive connection of each of said plurality of electrode surfaces to said current source; and
   successively repeating said measuring cycle.

4. A method as claimed in claim 1 wherein the step of measuring the resulting current is defined by the steps of:
   measuring the resulting current from a first of said at least two remaining electrode surfaces to obtain a first measurement result;
   storing said first measurement result; and
   measuring the resulting current from a second of said at least two remaining electrode surfaces to obtain a second measured result;
   and wherein the step of measuring the further resulting current is defined by the steps of:
   measuring the further resulting current at a first of said two of said further remaining electrode surfaces to obtain a further first measurement result;
   storing said further first measurement result; and
   measuring the resulting current at a second of said further remaining electrode surfaces to obtain a further second measurement result.

5. A method as claimed 1 wherein the step of measuring the resulting current is further defined by simultaneously measuring the resulting current at each of said at least two of said remaining electrode surfaces, and wherein the step of measuring the further resulting current is further defined by simultaneously measuring the further resulting current at at least two of said further remaining electrode surfaces.

6. A method as claimed in claim 1 wherein step (a) is further defined by connecting a first of said electrode surfaces to an alternating current source, wherein step (b) is further defined by measuring the impedance between said first electrode surface and said at least two of said remaining electrode surfaces to obtain at least two impedance measurements, wherein step (c) is further defined by comparing said at least two impedance measurements for equality, wherein step (d) is further defined by generating an alarm signal if said impedance measurements differ by more than a predetermined deviation, wherein step (e) is further defined by connecting said second electrode surface to said alternating current source, wherein step (f) is further defined by measuring the impedances between said second electrode surface and said at least two of said further remaining electrode surfaces to obtain at least two further impedance measurements, wherein step (g) is further defined by comparing said further impedance measurements of equality, and wherein step (h) is further defined by generating an alarm signal if said impedance measurements differ by more than a predetermined deviation.

7. A circuit for monitoring a neutral electrode of an HF surgery device, said neutral electrode having a plurality of electrode surfaces, for planar adjacency against body tissue of a patient, said circuit comprising:
   a current source;
   means for measuring current;
   first switching means for successively connecting said means for measuring current to each of said plurality of electrode surfaces;
   second switching means for successively connecting at least two of said plurality of electrode surfaces to said current source such that an electrode surface connected to said current source is not simultaneously connected to said means for measuring current, connection of one of said electrode surfaces to said current source causing a resulting current to arise at each of the remaining electrode surfaces, said resulting currents at each at said remaining electrode surfaces being measured by said means for measuring current;
   means for comparing the resulting current measured by said means for measuring current for equality; and
   means for generating an alarm signal is said resulting currents which are compared differ by more than a predetermined deviation.

8. A circuit as claimed in claim 7 further comprising a common electronic control means for operating said first and second means for switching.

9. A circuit as claimed in claim 8 wherein said first and second means for switching and said means for controlling form a single structural unit and further comprising a plurality of electrical lines corresponding in number to said plurality of electrode surfaces adapted for respectively connecting said electrode surfaces to said structural unit.

10. A circuit as claimed in claim 7 wherein said current source is an alternating current source, and wherein said means for measuring current is a means for measuring impedance of the body tissue of said patient between the electrode surface connected to said alternating current source and said remaining electrode surfaces.

11. A circuit as claimed in claim 7 wherein said first means for switching includes two banks of switches adapted for respective connection to said plurality of electrode surfaces and wherein said means for measuring current comprises two measuring units respectively connected to said banks of switches in said first means for switching.

* * * * *